United States Patent [19]
Matsuhashi et al.

[11] Patent Number: 4,939,239
[45] Date of Patent: Jul. 3, 1990

[54] HYPOSENSITIZATION AGENT OF CEDAR POLLEN ANTIGEN

[75] Inventors: Tyoku Matsuhashi, Saitama; Mitsuko Usui, Okayama; Masakazu Mitsuhashi, Okayama; Shunsaku Ando, Okayama, all of Japan

[73] Assignee: Kabushiki Kaisha Hayashibara Seitbutsu Kangaku/Kenkyujo, Okayama, Japan

[21] Appl. No.: 240,347

[22] Filed: Sep. 1, 1988

[30] Foreign Application Priority Data

Sep. 12, 1987 [JP] Japan .................................. 62-228781
Jul. 26, 1988 [JP] Japan .................................. 63-184487

[51] Int. Cl.$^5$ ............................................. A61K 39/36
[52] U.S. Cl. ...................................... 530/370; 424/91; 530/359; 530/379; 530/406
[58] Field of Search ............... 530/359, 370, 406, 379; 424/91

[56] References Cited

U.S. PATENT DOCUMENTS 4,185,090  1/1980  McIntire ......................... 530/359 X
4,432,969  2/1984  Batchelor ............................. 424/91

OTHER PUBLICATIONS

"Isolation and Partial Characterization of the Allergin in Mountain Cedar Pollen"; Gross et al; Chemical Abstracts vol. 90 No. 5; p. 374; 01/29/79.

Patent Abstracts of Japan; "Modified Antigen, Its Preparation and Preventive Remedy For Allergic Disease Containing The Same", Torii Yakuhin K.K., vol. 8, No. 171 (C-271), Jan. 16, 1985.

*Primary Examiner*—Howard E. Schain
*Attorney, Agent, or Firm*—Browdy and Neimark

[57] ABSTRACT

A novel hyposensitization agent was prepared by covalently attaching a saccharide, e.g. homo- and heteroglycans, for example, starch, amylose, dextran, polysucrose, pullulan, elsinan, curdlan, gum arabic, gum tragacanth, guar gum, xanthan gum carrageenan, pectin, cellulose, glucomannan, chitosan, and lipopolysaccharide, and their derivatives and partial hydrolysates to, a cedar pollen allergen. The hyposensitization agent can be administered to a cedar pollinosis patient without fear of eliciting anaphylaxis and allergy within a shortened hyposensitization period because the hyposensitization agent much more enhances the production of immunoglobulin G and M antibodies which are specific to intact cedar pollen allergen, but extremely reduces the production of immunoglobulin E antibody which is specific to the allergen and responsible for anaphylaxis and allergy.

6 Claims, No Drawings

HYPOSENSITIZATION AGENT OF CEDAR POLLEN ANTIGEN

BACKGROUND OF THE INVENTION

1. Field of the invention

The present invention relates to a hyposensitization agent. More particularly, the present invention relates to a hyposensitization agent comprising a cedar pollen allergen covalently attached to a saccharide.

2. Abbreviations

Ala: alanine residue
Arg: arginine residue
Asn: asparagine residue
Asp: aspartic acid residue
Gln: glutamine residue
Gly: glycine residue
Ile: isoleucine residue
Lys: lysine residue
Met: methionine residue
Pro: proline residue
Ser: serine residue
Trp: tryptophan residue
Each amino acid residue is in L-configuration.

3. Description of the prior art

Cedar pollinosis is an allergic disease caused by a cedar pollen scattered from blooming cedars.

Recently, the number of cedar pollinosis patients is gradually increasing in Japan with the increment of areas under cedar forestation. Although cedar pollinosis seasonally occurs, it is not insignificant in view of the public health.

In conventional therapy, for example, a steroid hormone or disodium cromolicate is administered. Such therapy is a symptomatic treatment which temporally relieves patient's symptom.

Administration of intact cedar pollen allergen responsible for cedar pollinosis has been attempted to effect hyposensitization in order to completely cure cedar pollinosis. Such hyposensitization has the drawbacks that it has a fear of eliciting anaphylaxis from the cedar pollen allergen used, and that treatment using the cedar pollen allergen should be continued for long time, i.e. about 3 years, because a small amount of the cedar pollen allergen is repeatedly administered to a cedar pollinosis patient in order to avoid such anaphylaxis.

Furthermore, cedar pollen allergen should be carefully handled because it is readily adsorbed on vessels such as glassware and metalware, and, in hyposensitization, this renders the administration of a prescribed amount of cedar pollen allergen very difficult.

SUMMARY OF THE INVENTION

The present inventors studied modification of cedar pollen allergen in order to obtain a novel hyposensitization agent which can be used in the prevention and treatment of cedar pollinosis.

As a result, the present inventors found that a hyposensitization agent comprising a cedar pollen allergen covalently attached to a saccharide can attain the object of the present invention.

DETAILED DESCRIPTION OF THE INVENTION

The cedar pollen allergen as referred to in the present invention includes those prepared from pollens of Japanese cedars (*Cryptomeria japonica*) such as "Omote Sugi (original type of Japanese cedar)" and "Ura Sugi (sub-species of Japanese cedar)", preferably, those having a partial amino acid sequence of Asp-Asn-Pro-Ile-Asp-Ser-, more particularly, Asp-Asn-Pro-Ile-Asp-Ser-X-Trp-Arg-Gly-Asp-Ser-Asn-Trp-Ala-Gln-Asn-Arg-Met-Lys- (wherein X is Ser, Cys, Thr or His) beginning at its N-terminal.

The saccharides usable in the present invention include homo- and hetero-glycans, for example, starch, amylose, dextran, polysucrose, pullulan, elsinan, curdlan, gum arabic, gum tragacanth, guar gum, xanthan gum, carrageenan, pectin, cellulose, glucomannan, chitosan, and lipopolysaccharide, and their derivatives and partial hydrolysates, having an average molecular weight in the range of 500–10,000,000, preferably, in the range of 10,000–1,000,000.

A hyposensitization agent comprising a cedar pollen allergen covalently attached to a water-soluble nonionic polysaccharide, mainly composed of repeating maltotriose units, such as pullulan, elsinan and their partial hydrolysates prevents an anaphylaxis which may be induced by intact cedar pollen allergen, as well as facilitating the preparation of a more effective hyposensitization agent of cedar pollinosis.

A hyposensitization agent comprising a cedar pollen allergen covalently attached to a hetero-glycan such as lipopolysaccharides derived from microorganisms, for example, a microorganism of the genus *E. coli, Salmonella* or *Serratia*, and their partial hydrolysates is favorably used as a hyposensitization agent for percutaneous and permucocutaneous administrations of cedar pollinosis because it is excellently bound to tissue such as mucous membranes.

Any procedure can be employed in the present invention as long as it forms a covalent bond between a cedar pollen allergen and a saccharide, for example, diazo coupling-, peptide-, alkylation-, cross-linking-, disulfide-coupling-, amide-bonding-, and periodate-oxidation-methods.

In the diazo coupling method, a cedar pollen allergen is allowed to react with an activated saccharide obtained by introducing an aromatic amino group, for example, p-aminobenzyl-, p-aminobezoyl-, m-aminobenzyl-, m-aminobezoyl-, m-aminoanisole-, m-aminobenzyloxy methyl-, 3-(p-aminophenoxy)-2-hydroxy-propionyl- and 3-(p-amino-m-methyl anilino)-5-chloro-triazinyl-groups into a saccharide in conventional manner.

In the peptide method, a cedar pollen allergen is allowed to react with an activated saccharide, such as sugar carbonate and cyanogen bromide-activated saccharide, which is a derivative of a saccharide bearing a carboxyl group obtained by allowing it to react with azide, acid chloride, carbodiimide or isocyanate.

In the alkylation method, a cedar pollen allergen is allowed to react with an alkyl halide derivative of a saccharide which has been introduced with a group, for example, chloroacetyl-, bromoacetyl-, iodoacetyl- and triazinyl-halide-groups.

In the cross-linking method, a cedar pollen allergen is allowed to react with a saccharide together with a polyfunctional reagent, for example, glutaraldehyde, glyoxal, succinaldehyde, hexamethylene diisocyanate, toluene-2,4-diisocyanate, bis-azobenzidine and N,N'-ethylene-bis-maleimide.

In the amide-bonding method, a cedar pollen allergen is allowed to react with an activated saccharide which has been obtained by reacting a saccharide having an amide group with haloacylhalide, for example, bromoacetylbromide, chlorobutyrylchloride, fluoropropionylfluoride and iodevaleryliodide.

The weight ratio of the cedar pollen allergen to the saccharide, both used in the covalent attachment, is usually in the range of 1:0.001–1:1,000, preferably, in the range of 1:0.01–1:100.

Any reaction conditions can be employed as long as the formation of a cedar pollen allergen-saccharide conjugate substantially does not reduce the production of immunoglobulin G and M antibodies which are specific to intact cedar pollen allergen, but extremely reduces the production of immunoglobulin E antibody which is responsible for anaphylaxis and allergy; usually, at a temperature of about 0–100° C. and a pH of about 3–12 for about 0.1–50 hours.

The cedar pollen allergen-saccharide conjugate thus obtained is usually separated and purified by conventional method, for example, filtration, washing, centrifugation, salting-out, dialysis, adsorption and desorption using ion exchange, gel filtration, ion exchange chromatography, affinity chromatography and electrophoresis into a solution and syrup, which can be dried into powder, if necessary. Thus, a hyposensitization agent of cedar pollinosis is obtained.

The hyposensitization agent can be advantageously used intact or, if necessary, in combination with a stabilizer, antiseptic agent, adjuvant and vehicle as an agent in the prevention and treatment of cedar pollinosis.

In comparison with conventional cedar pollen allergen, the hyposensitization agent prepared in this way much more enhances the producibilities of immunoglobulin G and M antibodies which are specific to intact cedar pollen allergen, but extremely reduces the producibility of immunoglobulin E antibody which is specific to the allergen and responsible for anaphylaxis and allergy. Administration of the hyposensitization agent to a cedar pollinosis patient elicits the minimum level of immunoglobulin E antibody which is specific to the allergen.

In comparison with intact cedar pollen allergen, the hyposensitization agent according to the present invention has the following advantages: that it is scarcely wasted because it does not adsorb on vessels such as glassware and metalware, that it is excellently stable, that it is administerable without fear of eliciting anaphylaxis, and that reduces the it hyposensitization sensitization period to about 1/3 to 1/200 of what is normally required.

The hyposensitization agent according to the present invention is usually prepared into an injection, for example, lyophilized injection or liquid injection, and then intradermally, subcutaneously, intramuscularly or intraperitoneally administered to a cedar pollinosis patient at a dose in the range of about 0.01–100,000 ng/shot/adult about 1–2 times/week over a period of about 1–12 months to attain a prescribed hyposensitization.

Furthermore, the hyposensitization agent can be prepared into a form which is advantageous for percutaneous and permucocutaneous administrations, for example, troche, sublingual, tablet, ophthalmic solution, intranasal nebula, cataplasma, cream and lotion. For example, the dose and administration frequency thereof are selected such that a prescribed hyposensitization is most readily attainable.

In a local administration such as percutaneous and permucocutaneous administrations, the hyposensitization agent can inhibit the binding between a cedar pollen allergen and immunoglobulin E antibody which has been bound to a cedar pollinosis patient's tissue. Such action is instantly and locally occurred at area where the hyposensitization agent has been administered. Thus, the hyposensitization agent instantly relieves the patient's pain.

The hyposensitization agent can be favorably used in the prevention and treatment of cedar pollinosis elicited by "Hinoki (*Chamaecyparis obtusa*)", as well as by cedar.

The following experiments will explain the present invention in more detail.

EXPERIMENT I-1

Preparation of cedar pollen allergen

A cedar pollen collected from "Omote Sugi" grown in Chiba, Japan, was added with about 15-folds by weight of 0.125 M aqueous sodium hydrogencarbonate solution (pH 8.0). The mixture was subjected to 1 hour extraction at 4° C. under gentle stirring conditions, followed by centrifugal separation. The residue was further subjected to extraction and centrifugal separation similarly as above. The resultant supernatants were pooled and salted out by the addition of ammonium sulphate to give 80% saturation, and the resultant precipitate was dialyzed and filtered. The filtrate was subjected to column chromatography using DEAE-Sephadex ®, commercialized by Pharmacia LKB Biotechnology AB, Uppsala, Sweden. The unadsorbed fraction was collected, subjected to column chromatography using CM-Sephadex ®, commercialized by Pharmacia LKB Biotechnology AB, Uppsala, Sweden, and eluted with phosphate buffered saline (pH 7.0). Then, the resultant solution was subjected to column chromatography using Mono S ®, commercialized by Pharmacia LKB Biotechnology AB, Uppsala, Sweden, and eluted with Tris-HCl buffer (pH 7.0) to separate a solution containing a purified cedar pollen allergen exhibiting a high affinity to immunoglobulin E antibody of a cedar pollinosis patient, as well as to anti cedar pollen allergen mouse monoclonal antibody in the yield of about 0.02% against the material cedar pollen based on dry solid.

The cedar pollen allergen exhibited a molecular weight of about $50,000 \pm 5,000$ on SDS-polyacrylamide gel electrophoresis, and an isoelectric point of about 8.8.

A partial amino acid sequence of the cedar pollen allergen was obtained by degrading it with a gas-phase protein sequencer and identifying the resultant with high-performance liquid chromatography by the method described in *The Journal of Biological Chemistry*, Vol. 256, pp. 7990–7997 (1981). As a result, it was found that the cedar pollen allergen had a partial amino acid sequence of Asp-Asn-Pro-Ile-Asp-Ser-X-Trp- Arg-Gly-Asp-Ser-Asn-Trp-Ala-Gln-Asn-Arg-Met-Lys-(wherein X is Ser, Cys, Thr or His).

EXPERIMENT I-2

Preparation of cedar pollen allergen-pullulan conjugate

One hundred milliliters of 2 w/v % pullulan aqueous solution, average molecular weight of 300,000, was added with 2 ml of 1.7 w/v % cyanuric chloride in acetone. The mixture solution was allowed to stand at 5° C. or lower in ice-chilled water, adjusted to pH 7.0 by the addition of 5% sodium carbonate aqueous solution, and allowed to react for 2 hours while retaining the temperature and pH. Then, the reaction mixture was dialyzed overnight against 4° C. water while retaining the pH. Thus, an activated-pullulan solution was obtained. Thirty milliliters of the activated-pullulan solution was added with 40 ml of a solution containing about 1 mg/ml of a purified cedar pollen allergen obtained by the method in Experiment I-1. The resultant mixture was allowed to stand first at pH 7.0 and 37° C. for 5 hours while stirring, then at 5° C. overnight, followed by the addition of 6 g glycine. The resultant mixture was allowed to stand for 10 hours while stirring, dialyzed against 0.01 M acetate buffer (pH 5.0), and subjected to column chromatography using CM-Sephadex ®. The unadsorbed fraction was membrane-filtered to obtain an allergen-pullulan conjugate.

The yield was about 60% against the cedar pollen allergen protein. Unlike intact cedar pollen allergen, the product is easily handleable because it is excellently stable and because it is scarcely wasted by its adsorption on glassware and metalware.

EXPERIMENT I-3

Administration test on animal

EXPERIMENT I-3-1

Test on prophylactic activity 0.2 ml of physiological saline containing as an allergen 1 μg of an allergen-pullulan conjugate obtained by the method in Experiment I-2 was intraperitoneally administered to a group of six 10 to 12 week-old BALB/c female mice once a week over a period of 3 weeks. One week after the intraperitoneal administration, 0.2 ml of physiological saline containing 1 μg of a cedar pollen allergen, obtained by the method in Experiment I-1, and 4 mg aluminum hydroxide as an adjuvant was administered to each mouse in the same manner as described in the above.

The amounts of immunoglobulin G, M and E antibodies which were specific to intact cedar pollen allergen were determined with a blood sample which had been collected from mice immediately before the intraperitoneal administration of the mixture of cedar pollen allergen and aluminum hydroxide, and another blood sample which had been collected from the mice 1-week after the intraperitoneal administration of the mixture.

As control, a mixture containing 1 μg of a cedar pollen allergen prepared by the method in Experiment I-1 and 40 μg of a fresh preparation of the same pullulan as used in Experiment I-2 was administered to each mouse in place of the allergen-pullulan conjugate.

The levels of immunoglobulin G and M antibodies were compared with their antibody titers determined by the technique for passive hemagglutination reaction described in *Japanese Journal of Medical Science and Biology*, Vol. 28, pp. 127–138 (1975), and the level of immunoglobulin E antibody was compared with its antibody titer determined by the passive cutaneous anaphylaxis reaction described in Life Science, Vol. 8, Part II, pp. 813–820 (1969). The results were as shown in Table 1.

TABLE 1

| | Period for collecting blood | | | | |
| --- | --- | --- | --- | --- | --- |
| | Immediately before administration of mixture of cedar pollen allergen and aluminum hydroxide | | One week after administration of mixture of cedar pollen allergen and aluminum hydroxide | | |
| | Immunoglobulin | | | | |
| Hyposensitization agent | G & M | E | G & M | E | Note |
| Cedar pollen allergen-pullulan conjugate | 240 | 0 | 940 | 5 | Present invention |
| Mixture of cedar pollen allergen and pullulan | 25 | 20 | 250 | 320 | Control |

Annotation: Each value is an average of immunoglobulin antibody titers of immunoglobulin antibodies produced in a group of 6 mice.

As evident from the results in Table 1, unlike the mixture of cedar pollen allergen and pullulan, the cedar pollen allergen-pullulan conjugate according to the present invention can be favorably used as a hyposensitization agent in the prevention of cedar pollinosis.

EXPERIMENT I-1-3-2

Test on therapeutic activity 0.2 ml of physiological saline containing a mixture of 1 μg of a cedar pollen allergen obtained by the method in Experiment I-1 and 4 mg aluminum hydroxide as an adjuvant was intraperitoneally administered to a group of six 10 to 12 week-old BALB/c female mice once a week over a period of 3 weeks. Two weeks after the intraperitoneal administration, 0.2 ml of physiological saline containing as an allergen 1 μg of a cedar pollen allergen-pullulan conjugate obtained by the method in Experiment I-2 was administered in the same manner as described in the above to each mouse three times a week over a period of 3 weeks.

Formation of immunoglobulin E antibody was boosted by administering a mixture of cedar pollen allergen and aluminum hydroxide to the mice.

The levels of immunoglobulin G, M and E antibodies were determined with a blood sample collected from mice just before and 1-week after the final intraperitoneal administration of the cedar pollen allergen-pullulan conjugate, and another blood sample which had been collected from mice one week after the induction of immunoglobulin E antibody by the intraperitoneal administration of the mixture of cedar pollen allergen and aluminum hydroxide.

As control, a mixture of cedar pollen allergen and pullulan was used similarly as in Experiment I-3-1 in place of the cedar pollen allergen-pullulan conjugate. The results were as shown in Table 2.

TABLE 2

| Hyposensitization agent | Period collecting blood | | | | | | |
|---|---|---|---|---|---|---|---|
| | Immediately before administration of cedar pollen allergen-pullulan conjugate | | One week after administration of cedar pollen allergen-pullulan conjugate | | One week after production of immunoglobulin E antibody by booster shot | | |
| | Immunoglobulin | | | | | | |
| | G & M | E | G & M | E | G & M | E | Note |
| Cedar pollen allergen-pullulan conjugate | 350 | 160 | 2,300 | 30 | 5,840 | 30 | Present invention |
| Mixture of cedar pollen allergen and pullulan | 350 | 160 | 480 | 320 | 2,870 | 1,280 | Control |

Annotation: Each value is an average of immunoglobulin antibody titers of immunoglobulin antibodies produced in a group of 6 mice.

As evident from the results in Table 2, unlike a mixture of cedar pollen allergen and pullulan, the cedar pollen allergen-pullulan conjugate according to the present invention can be favorably used as a hyposensitization agent in the treatment of cedar pollinosis.

Mice which had been previously primed with a mixture of cedar pollen allergen and aluminum hydroxide to produce immunoglobulin E antibody were sprayed with a physiological saline containing the cedar pollen allergen-pullulan conjugate into their mouths and nasal cavities. One hour after the spraying, the mice were resprayed with intact cedar pollen allergen into their mouths and nasal cavities, and the allergic reaction which would be elicited in the mice was not observed.

As described hereinbefore, a cedar pollen allergen-saccharide conjugate according to the present invention can be favorably used as a hyposensitization agent in the prevention and treatment of cedar pollinosis because the conjugate effects a high hyposensitivity without fear of eliciting anaphylaxis.

EXPERIMENT II-1

Preparation of cedar pollen allergen and lipopolysaccharide conjugate

One milliliter of 10 mM calcium phosphate solution containing 10 mg of a lipopolysaccharide derived from a microorganism of the species *E. coli* was added with 60 ml of 100 mM sodium periodate, and the mixture was allowed to react at ambient temperature for 20 minutes to cleave the specified bonding of the saccharide chain in the lipopolysaccharide. Then, the resultant mixture was dialyzed overnight against 1 M glycine-HCl buffer (pH 4.4) at 4° C. to remove an excess amount of sodium periodate. The resultant solution was adjusted to about pH 9.5 by the addition of 0.1 M sodium hydrogencarbonate buffer to prepare a lipopolysaccharide solution.

Ten milligrams of a cedar pollen allergen prepared by the method in Experiment I-1 was dissolved in 1 ml of phosphate buffer (pH 9.5), and the mixture was added with the lipopolysaccharide solution, followed by the formation of Schiff base of the cedar pollen allergen and the lipopolysaccharide.

The reaction mixture was added with sodium borohydride to complete coupling reaction. The resultant solution was subjected to column chromatography using Sephadex ® G-100, a product of Pharmacia LKB Biotechnology AB, Uppsala, Sweden, and the fraction containing a cedar pollen allergen-lipopolysaccharide conjugate was collected. The fraction was membrane-filtered to obtain the cedar pollen allergen-lipopolysaccharide conjugate.

The yield of the product was about 40% against the cedar pollen allergen protein.

Unlike intact cedar pollen allergen, the product is easily handleable and scarcely wasted because it does not adsorb on vessels such as glassware.

EXPERIMENT II-2

Administration test on animal Test on therapeutic activity

One milliliter of physiological saline containing as an allergen 10 μg of a cedar pollen allergen-lipopolysaccharide conjugate prepared by the method in Experiment II-1 was orally administered to a group of six 10 to 12 week-old BALB/c female mice three times a week over a period of 3 weeks. One week after the oral administration, blood samples were collected from the mice, and the amounts of immunoglobulin A, G and E antibodies which were specific to intact cedar pollen allergen were determined with the blood samples.

As control, a mixture of intact cedar pollen allergen and lipopolysaccharide was orally administered to mice similarly as above in place of the cedar pollen allergen-lipopolysaccharide conjugate. The levels of immunoglobulin A and G antibodies were compared with their antibody titers determined by the enzymoimmunoassay method described in *Journal of Immunological Methods*, Vol. 6, pp. 355–362 (1975), while the level of iimmunoglobulin E antibody was compared with its antibody titer determined by the passive cutaneous anaphylaxis reaction described in Experiment I-3-1. The results were as shown in Table 3.

TABLE 3

| Hyposensitization agent | Immunoglobulin | | | Note |
|---|---|---|---|---|
| | A | G | E | |
| Cedar pollen allergen-lipopolysaccharide conjugate | 256 | 64 | 0 | Present invention |
| Mixture of cedar pollen allergen and lipopolysaccharide | 4 | 16 | 16 | Control |

Annotation: Each value is an average of immunoglobulin antibody titers of immunoglobulin antibodies produced in a group of 6 mice.

As evident from the results in Table 3, unlike the mixture of cedar pollen allergen and lipopolysaccharide, the cedar pollen allergen-lipopolysaccharide conjugate according to the present invention can be favorably used as a hyposensitization agent in the prevention and treatment of cedar pollinosis.

Mice which had been previously primed with a mixture of cedar pollen allergen and aluminum hydroxide to produce immunoglobulin E antibody were sprayed with a physiological saline containing the cedar pollen allergen-lipopolysaccharide conjugate into their mouths and nasal cavities. Thirty minutes after the spraying, the mice were resprayed with intact cedar pollen allergen into their mouths and nasal cavities, and the allergic reaction which would be elicited in the mice was not observed.

A cedar pollen allergen-hetero glycan conjugate such as a cedar pollen allergen-lipopolysaccharide conjugate is superior in absorbability into mucous membranes to a cedar pollen allergen-homo glycan conjugate such as a cedar pollen allergen-pullulan conjugate because the cedar pollen allergen-lipopolysaccharide conjugate is adsorbed on the mucous membranes for a relatively long period of time. Because of the above reason, such cedar pollen allergen-hetero glycan conjugate is favorably used as a hyposensitization agent for percutaneous and permucocutaneous administrations such as oral and intranasal administrations.

Several embodiments according to the present invention will hereinafter be explained.

EXAMPLE 1

Example 1(1)

Preparation of cedar pollen allergen

A cedar pollen collected from "Ura Sugi" grown in Akita, Japan, was prepared into a purified cedar pollen allergen in solution by the method in Experiment I-1 in the yield of about 0.015% against the weight of the material cedar pollen based on dry solid. The purified cedar pollen allergen had a molecular weight of about 50,000±5,000 on SDS-polyacrylamide gel electrophoresis, and an isoelectric point of about 8.8.

After detecting a partial amino acid sequence of the cedar pollen allergen in accordance with the method in Experiment I-1, the partial amino acid sequence consisting of 20-amino acid residues beginning at its N-terminal was identical with that of the allergen prepared from "Omote Sugi" described in Experiment I-1.

Example 1(2)

Hyposensitization agent

Five grams of pullulan having an average molecular weight of about 140,000 was dissolved in 400 ml of water, and the resultant solution was adjusted to pH 10.7 by the addition of 1 N sodium hydroxide. The solution was then allowed to react with 3 g cyanogen bromide for 1 hour while gradually adding it to the solution and retaining the pH. The reaction mixture was adjusted to pH 5.0 by the addition of 1 N hydrochloric acid, and dialyzed against cold water while retaining the pH. Thus, an activated-pullulan solution was obtained.

To the activated-pullulan solution was added 200 ml of a cedar pollen allergen solution prepared by the method in Example 1(1), and the mixture was allowed to react at ambient temperature for 24 hours. After completion of the reaction, the reaction mixture was added with acetone (1:3 by volume) to obtain a precipitate which was then collected, dissolved in 0.01 M acetate buffer (pH 5.0), and centrifugally separated to remove the insoluble residue. The remaining supernatant was subjected to column chromatography using CM-Sephadex ®, and the unadsorbed fraction was membrane-filtered. The filtrate was bottled into ampules to obtain a liquid hyposensitization agent containing a cedar pollen allergen-pullulan conjugate.

The yield was about 70% against the cedar pollen allergen protein. The product can be favorably used in the prevention and treatment of cedar pollinosis because the product effects a high hyposensitivity without fear of eliciting anaphylaxis.

Unlike intact cedar pollen allergen, the product is easily handleable because it is excellently stable and because it is scarcely wasted by its adsorption on glassware and metalware.

EXAMPLE 2

Fifty-two grams of a pullulan partial hydrolysate, average molecular weight of about 10,000, was dissolved in 110 ml of dimethylformamide while heating. The mixture was cooled to ambient temperature, and added with 10 ml of pyridine. The resultant mixture was added with 1.0 g 4-nitrobenzoyl chloride while stirring, and allowed to stand at ambient temperature for 17 hours. The reaction mixture was added with 2-volumes of n-propyl alcohol to obtain a precipitate which was then collected and dissolved in dimethylformamide. The above precipitation was repeated 3-times, and the resultant precipitates were pooled and dissolved in 100 ml of 5 w/v % sodium hydrosulfite aqueous solution. The mixture was allowed to stand at 80° C. for 30 minutes, decolored with activated charcoal and precipitated with 2-volumes of n-propyl alcohol. The precipitate was dissolved in water, and the resultant solution was dialyzed overnight against water, cooled to 2° C. or lower, and added with hydrochloric acid to give a final concentration of about 0.1 N while stirring. Then, the resultant mixture was added with sodium nitrite to give a concentration of about 1 w/v %, allowed to react for 30 minutes, and dialyzed against distilled water at 2° C. or lower for 2 hours to obtain an activated pullulan partial hydrolysate.

To the activated pullulan partial hydrolysate was added 20 ml of a solution containing a cedar pollen allergen from "Omote Sugi" obtained by the method in Experiment I-1, and the mixture was adjusted to pH 8.5 by the addition of a sodium carbonate aqueous solution. Then, the mixture was allowed to effect coupling reaction at 4° C. for 2 hours while stirring, purified similarly as in Example 1, and bottled into ampules to obtain a liquid hyposensitization agent containing a cedar pollen allergen-pullulan partial hydrolysate conjugate.

The yield was about 60% against the cedar pollen allergen protein.

Similarly as the product in Example 1, the liquid hyposensitization agent is favorably used in the prevention and treatment of cedar pollinosis and is easily handleable because it is excellently stable and because it is scarcely wasted by its adsorption on glassware and metalware.

EXAMPLE 3

Ten grams of elsinan, average molecular weight of about 200,000, was dissolved in 200 ml of distilled water while heating. The resultant was cooled to ambient temperature and added with 5 g hexamethylenediamine. The mixture solution was adjusted to pH 11.0 by the addition of 1 N sodium hydroxide solution, allowed to stand at 20° C. or lower in ice-chilled water, and added with 5 g cyanogen bromide while retaining the temperature and pH. The resultant mixture was allowed to react for 30 minutes while stirring and retaining the temperature and pH. The reaction mixture was dialyzed against 4° C. distilled water for 1 hour to obtain an activated-elsinan solution.

The activated-elsinan solution was added with 2 ml of 25 w/v % glutaraldehyde and 60 ml of a solution containing a cedar pollen allergen from "Omote Sugi" obtained by the method in Experiment I-1, and the mixture was added with 10 ml of 1 M acetate buffer (pH 5.0) to effect coupling reaction at 4° C. for 24 hours while stirring. The reaction mixture was added with glycine to give a concentration of 1 M, and the resultant was allowed to stand at ambient temperature for 24 hours, and then subjected to centrifugal separation. The supernatant was subjected to gel filtration, and a fraction containing a cedar pollen allergen-elsinan conjugate was collected. The fraction was concentrated and membrane-filtered. The filtrate was bottled, lyophilized and sealed to obtain a solid hyposensitization agent containing the cedar pollen allergen-elsinan conjugate.

The yield was about 50% against the cedar pollen allergen protein.

Similarly as the product in Example 1, the product is easily handleable and usable in the prevention and treatment of cedar pollinosis.

EXAMPLE 4

Two hundred milliliters of 1 w/v % carboxymethyl cellulose solution, average molecular weight of about 20,000, was added with 2 g 1-ethyl-3-(3-dimethylaminopropyl)-carbodiimide-methiodide, and the mixture solution was adJusted to pH 4.0 and allowed to react at ambient temperature for 2 hours while stirring and retaining the pH. The reaction mixture was dialyzed overnight against distilled water to obtain an activated-carboxymethyl-cellulose solution.

The activated-carboxymethyl-cellulose solution was added with 50 ml of a solution containing a cedar pollen allergen from "Ura Sugi" obtained by the method in Example 1(1), and the activated carboxymethyl cellulose and the cedar pollen allergen were allowed to effect coupling reaction at ambient temperature overnight while stirring and retaining pH at 4.5. Then, the resultant conjugate was purified similarly as the method in Example 3, and bottled into ampules to obtain a liquid hyposensitization agent containing the cedar pollen allergen-carboxymethyl cellulose conjugate.

The yield was about 30% against the cedar pollen allergen protein.

Although the product is slightly lower in production of immunoglobulin G and M antibodies which are specific to intact cedar pollen allergen than a cedar pollen allergen-pullulan conjugate and a cedar pollen allergen-elsinan conjugate, the product is easily handleable because it does not produce immunoglobulin E antibody which is specific to the allergen, and because it is usable as a hyposensitization agent in the prevention and treatment of cedar pollinosis.

EXAMPLE 5

One hundred milligrams of a lipopolysaccharide derived from a microorganism of the genus *Salmonella* was added with 25 ml of 50% saturated sodium acetate at about 4° C., and the mixture was adjusted to pH 9.0 by the addition of 0.5 N sodium hydroxide. To the resultant mixture was added dropwise a mixture solution (about pH 8.5) of 20 μl bromoacetylbromide and 1 ml anhydrous dioxane. The obtained mixture was adjusted to about pH 4.5 by the addition of 6 N hydrochloric acid, and dialyzed against 4° C. water for 5 days to obtain an activated-lipopolysaccharide solution. The activated-lipopolysaccharide solution was added with 40 ml of a cedar pollen allergen solution prepared by the method in Example 1(1), and the mixture was allowed to react at 25 ° C. for 2 days while stirring and retaining its pH at 4.5. The reaction mixture was purified similarly as in Example 3, and bottled into ampules to obtain a liquid hyposensitization agent containing a cedar pollen allergen-lipopolysaccharide conjugate.

The yield of the product was about 35% against the cedar pollen allergen protein.

The product is easily absorbed into mucous membranes because it is excellently bound to them and locally adsorbed on them for a relatively long period of time. The product is an excellent hyposensitization agent of cedar pollinosis for percutaneous and permucocutaneous administrations such as oral and intranasal administrations.

Effect of the invention

As evident from the above, a hyposensitization agent comprising a cedar pollen allergen covalently attached to a saccharide is administrable to a cedar pollinosis patient without fear of eliciting anaphylaxis, and the hyposensitization period to about 1/3 to 1/200 because the hyposensitization agent greater accelerates the production of immunoglobulin G and M antibodies which are specific to intact cedar pollen allergen, but greater reduces the production of immunoglobulin E antibody which is specific to the allergen.

The hyposensitization agent according to the present invention is favorably used as an agent for local administrations such as percutaneous and permucocutaneous administrations because the hyposensitization agent inhibits the antigen-antibody reaction between immunoglobulin E antibody which has been bound to a cedar pollinosis patient's tissue and intact cedar pollen allergen, and instantly relieves the patient's pain.

Furthermore, the hyposensitization agent according to the present invention has a great significance in the field because it is scarcely wasted because it does not adsorb on vessels such as glassware and metalware, that it is excellently stable, and that it is easily handleable as compared with intact cedar pollen allergen.

While there has been described what is at present considered to be the preferred embodiments of the invention, it will be understood that various modifications may be made therein, and it is intended to cover in the appended claims all such modifications as fall within the true spirit and scope of the invention.

We claim:

1. A hyposensitization agent for the prevention and-/or treatment of cedar pollinosis comprising a cedar pollen allergen, said cedar pollen allergen comprising a partial amino acid sequence of Asp-Asn-Pro-Ile-Asp-Ser-beginning at the N-terminal of said cedar pollen allergen; and a saccharide covalently attached to said cedar pollen allergen, said saccharide being a member selected from the group consisting of homo- and heteroglycans.

2. The agent as claimed in claim 1, wherein said cedar pollen allergen comprises a partial amino acid sequence of Asp-Asn-Pro-Ile-Asp-Ser-X-Trp-Arg-Gly-Asp-Ser-Asn-Trp-Ala-Gln-Asn-Arg-Met-Lys-(wherein X is Ser, Cys, Thr or His) beginning at the N-terminal of said cedar pollen allergen.

3. The agent as claimed in claim 1, wherein said cedar pollen allergen can be prepared from a pollen of *Cryptomeria japonica*.

4. The agent as claimed in claim 1, wherein said saccharide is a polysaccharide mainly composed of repeating maltotriose units.

5. The agent as claimed in claim 1, wherein said saccharide is a lipopolysaccharide.

6. The agent as claimed in claimed in claim 1, wherein said agent is for treatment of cedar pollinosis.

* * * * *